United States Patent [19]

Le

[11] Patent Number: 5,173,983
[45] Date of Patent: Dec. 29, 1992

[54] ELECTRIC TOOTHBRUSH HAVING SPIRALLY ARRANGED BRISTLES

[76] Inventor: Mike Le, c/o Hung Hsing Patent Service Center, P.O. Box 55-1670, Taipei (10477), Taiwan

[21] Appl. No.: 710,110

[22] Filed: Jun. 4, 1991

[51] Int. Cl.⁵ .................. A61C 17/26; A46B 13/02; A46B 9/04
[52] U.S. Cl. .......................................... 15/28; 15/180
[58] Field of Search .............. 15/23, 28, 29, 97.1, 15/180; 433/114, 124, 125, 130

[56] References Cited

U.S. PATENT DOCUMENTS

| 2,093,007 | 9/1937 | Chott | 15/28 |
| 3,757,419 | 9/1973 | Hopkins | 15/28 |
| 3,802,420 | 4/1974 | Moffat et al. | 15/28 |
| 3,848,336 | 11/1974 | Copeland | 15/28 |
| 4,827,552 | 5/1989 | Bojar et al. | 15/28 |

FOREIGN PATENT DOCUMENTS

| 414971 | 9/1946 | Italy | 15/28 |
| 477799 | 1/1938 | United Kingdom | 15/28 |

Primary Examiner—Edward L. Roberts

[57] ABSTRACT

A toothbrush includes a bristle holder rotatably mounted on an end portion of a toothbrush handle and driven by an electric motor mounted inside the handle having a plurality of bristles spirally mounted on the bristle holder operatively driven for a rotation of the bristles for rotatably brushing, piercing and removing foods accumulated on teeth surfaces, or in apertures between the neighboring teeth for effectively cleaning a user's teeth.

3 Claims, 3 Drawing Sheets

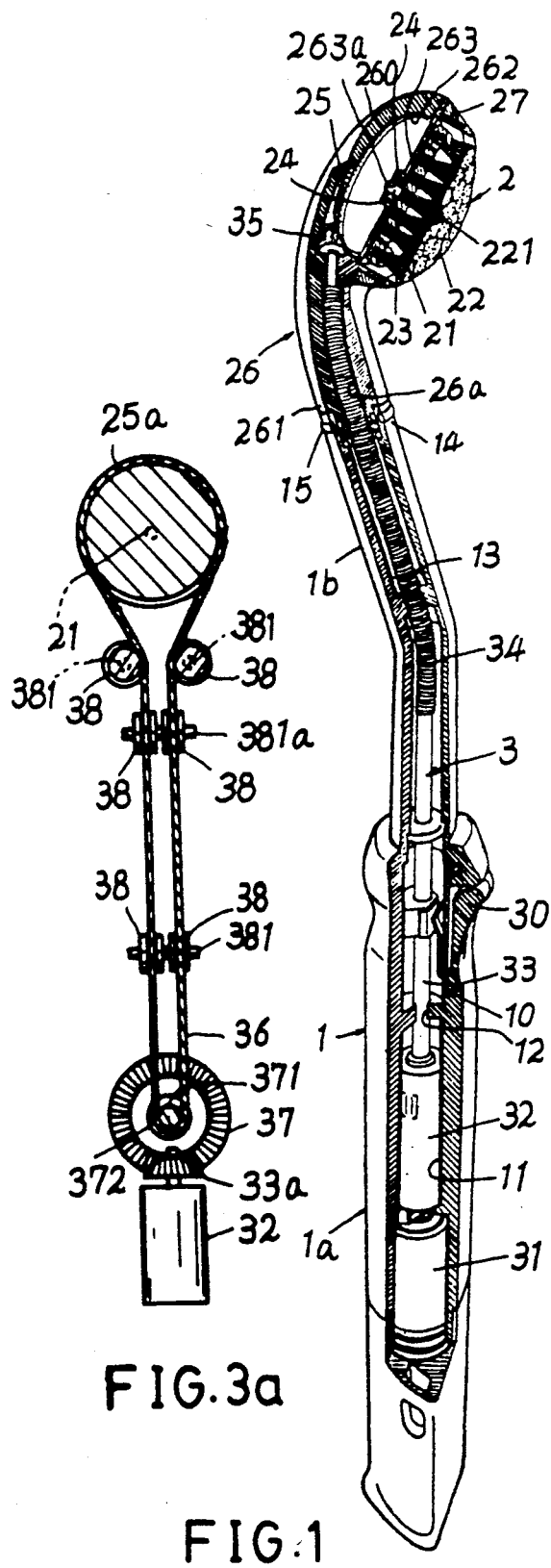
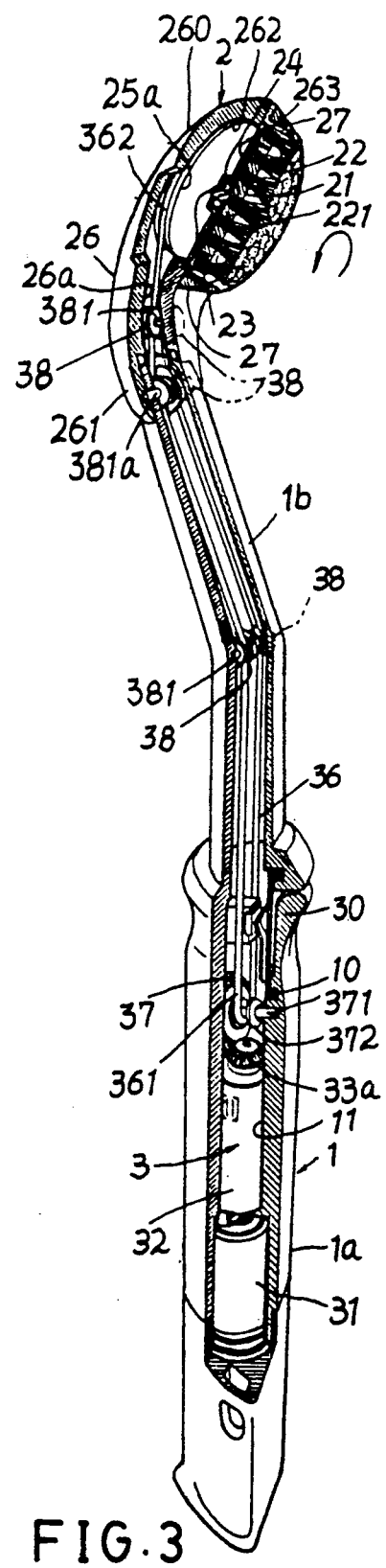
FIG.3a FIG.1 FIG.3

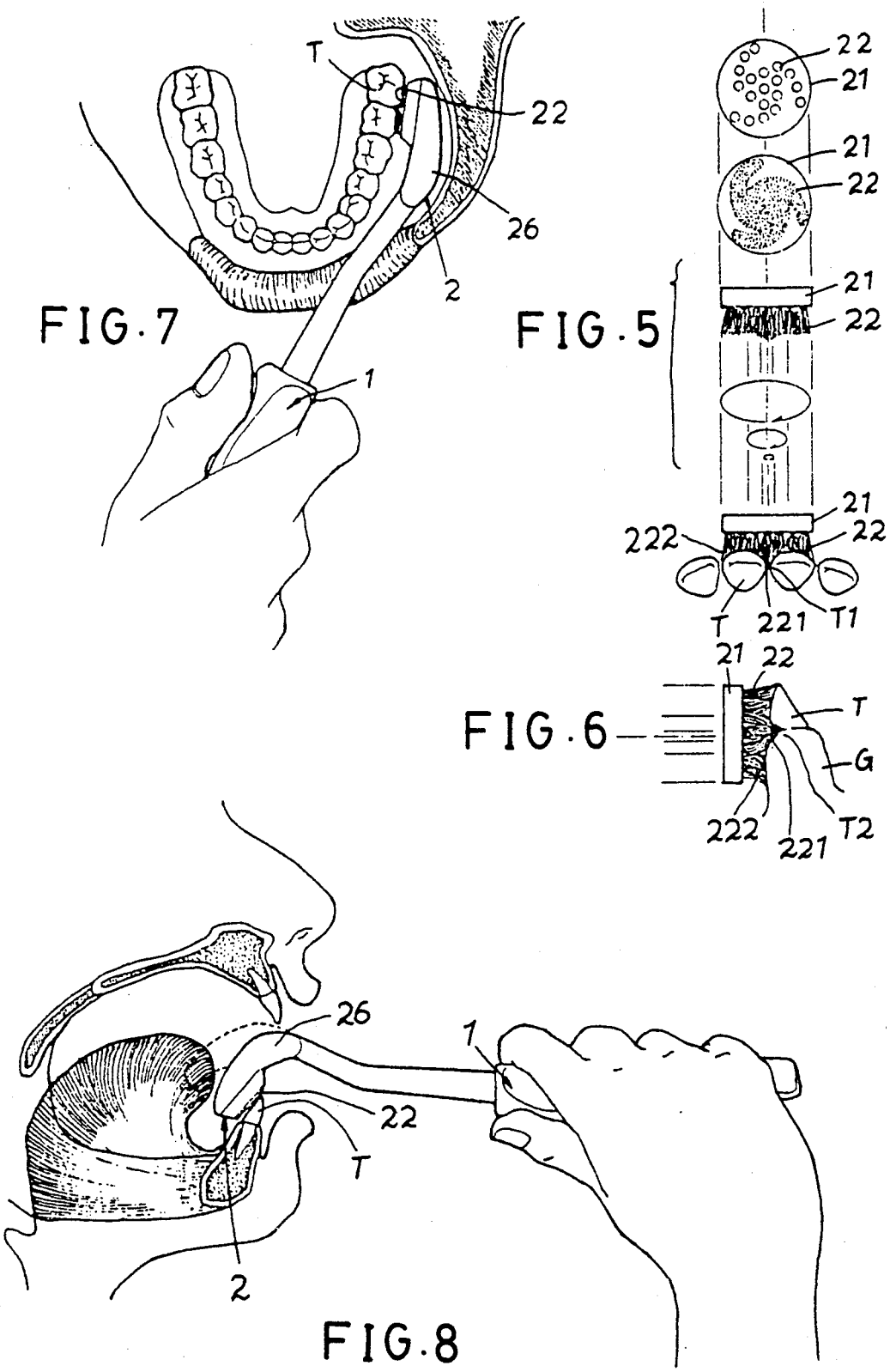

ELECTRIC TOOTHBRUSH HAVING SPIRALLY ARRANGED BRISTLES

BACKGROUND OF THE INVENTION

Massari disclosed a toothbrush with multi-positionable head in his U.S. Pat. No. 4,471,506 whose cleaning head can be set at various angles in relation to the handle for effectively cleaning a user's teeth.

However, its bristles 12 mounted on the cleaning head 10 are formed with plural bundles of bristles generally rectangular shaped and are used for brushing the teeth by repeated up or down movements on teeth surfaces. The foods accumulated in apertures between the neighbouring teeth still cannot be effectively removed by such up-and-down reciprocative brushing operations or by other reciprocative brushing movements at any oriented angles.

Therefore, the present inventor has invented a toothbrush which is electrically driven for rotably brushing or piercing teeth apertures or cavities for enhancing a tooth-cleaning function.

SUMMARY OF THE INVENTION

The object of the present invention is to provide a toothbrush including a bristle holder rotatably mounted on an end portion of a toothbrush handle and driven by an electric motor mounted inside the handle having a plurality of bristles planted on the bristle holder operatively driven for a spiral rotation of the bristles for rotably brushing, piercing and removing foods accumulated on teeth surfaces, or in apertures between the neighbouring teeth for effectively cleaning a user's teeth.

BRIEF DESCRIPTION OF THE DRAWINGS

FIG. 1 is a partial cut-away drawing of the present invention.

FIG. 3 is a partial cut-away illustration of another preferred embodiment of the present invention.

FIG. 3a shows a transmission system of a driving means of the toothbrush as shown in FIG. 3.

FIG. 5 shows a spiral arrangement of the bristles on the bristle base portion and their brushing operation in accordance with the present invention.

FIG. 6 shows another operation in accordance with the present invention.

FIG. 7 shows a cleaning operation by using the present invention inside a user's mouth.

FIG. 8 shows another cleaning operation inside a user's mouth.

DETAILED DESCRIPTION

Figure 2:
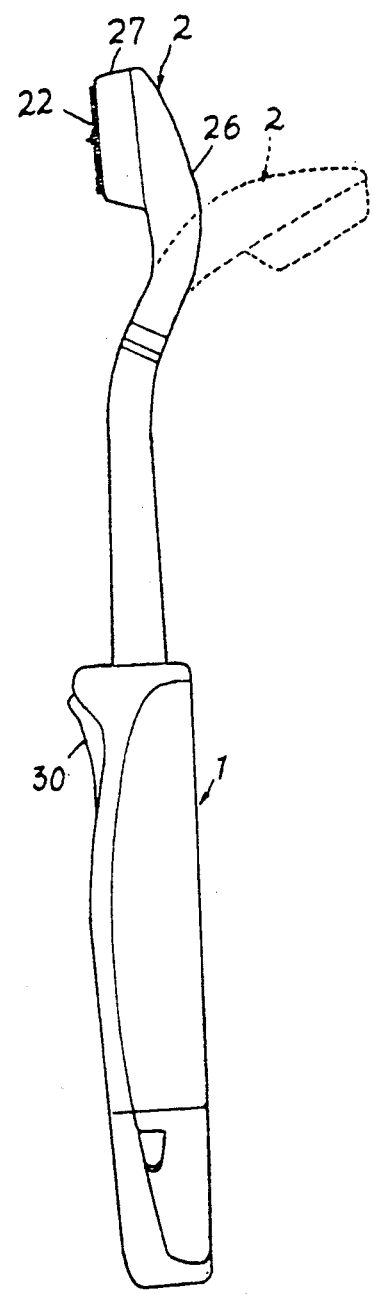
FIG. 2 is an illustration of the present invention when a bristle holder is rotated.

As shown in FIGS. 1 and 2, the present invention comprises: a handle 1, a bristle holder means 2, and a driving means 3.

The handle 1 includes: a grip portion 1a formed on a lower portion of the handle 1, an upper rod portion 1b connected with the grip portion 1a for rotatably securing the bristle holder means 2 thereon, an inner cavity 11 longitudinally formed inside the handle 1, a first sleeve portion 12 formed inside the grip portion 1a, a second sleeve portion 13 formed inside the upper rod portion 1b, and a swivel joint 15 formed on an upper end portion 14 of the upper rod portion 1b for rotatably coupling the handle 1 with the bristle holder means 2. The handle 1 may be formed as a generally straight shape or a slightly bent or arcuate shape, not limited in this invention.

The bristle holder means 2 includes: a bristle base portion 21 having a plurality of bristles 22 mounted thereon, an axle portion 23 protruding downwardly from the bristle base portion 21 to be rotatably mounted in a bristle holder 26 or mounted in an axle hole 263a formed in a supporting plate 263 secured on the bristle holder 26, a packing ring 24 sealably disposed around the axle portion 23 and the axle hole 263a of the supporting plate 263, a follower gear 25 formed as a bevel gear secured with the axle portion 23 rotatably held in a bristle socket 262 formed in a head portion 260 of the bristle holder 26, the bristle holder 26 having a central hole 26a formed therethrough and a lower end portion 261 rotatably coupled with the upper end portion 14 of the handle 1, and a soft protective wall 27 having a height of the wall 27 lower than a height of the bristle and circumferentially disposed on the head portion 260 for enclosing the bristles 22. The soft protective wall 27 also helps the user for sensing a "target" tooth for cleaning operation by touch feeling of the wall 27 on a tooth or gum portion.

The driving means 3 includes: a power source 31 which may be dry batteries or an adaptor by rectifying and transforming an alternative current (AC) from an AC power source stored in a lower portion of the cavity 11, a driving motor 32 electrically connected with the power source 31 and controlled by a switch 30 formed on the handle 1, a motor shaft 33 driven by the driving motor 32 rotatably secured in the first sleeve portion 12, a transmission shaft 34 which is preferably a flexible transmission shaft connected with the motor shaft 33 and rotatably secured in the second sleeve portion 13 and protruding upwardly inside the cavity 11 and the central hole 26a in the bristle holder 26, and a driving gear 35 formed as a bevel gear formed on an upper end of the flexible shaft 34 engageable with the follower gear 25 of the bristle holder means 2.

When the switch 30 is switched on to power the driving motor 32 to rotate the shafts 33, 34, the follower gear 25 and the bristle base portion 21 will be rotated to rotate the bristles 22 for cleaning a user's teeth as shown in FIGS. 5-8.

In FIG. 5, the bristles include a first portion of the bristles forming a central vertex bristle portion 221 penetrable into aperture T1 between two neighbouring teeth for piercing and removing foods accumulated therein and a second portion of the bristles forming a peripheral bristle portion 222 for rotatably brushing the teeth surfaces for effectively cleaning the teeth T.

As shown in FIG. 6, the vertex portion 221 of the bristles 22 serves for cleaning an aperture T2 between a tooth T and a gum G, whereas the peripheral portion 222 of the other bristles 22 may still clean the tooth surface and gum surface (also for massaging the gum G).

The present invention can be operated for adjusting a rotating angle of the bristle holder means 2 about the universal joint 15 as shown in FIG. 1 or about a pivot 381a as shown in FIG. 3 (which will be hereinafter described) to poke the bristles 22 deeply into an inner corner inside a user's mouth for cleaning an outer surface of a tooth T proximate a user's cheek side as shown in FIG. 7 or into an inner surface of the tooth T proximate a tongue as shown in FIG. 8.

Therefore, the present invention can be used for effectively cleaning a user's teeth, in which the bristles 22 mounted on the base portion 21 generally circular shaped will act like a drill or a grinder rotatably piercing any corner, aperture or cavity in a tooth surface or in between the neighbouring teeth, thereby thoroughly cleaning the teeth and being superior to any conventional toothbrush either manually operated or electrically driven.

Figure 4:
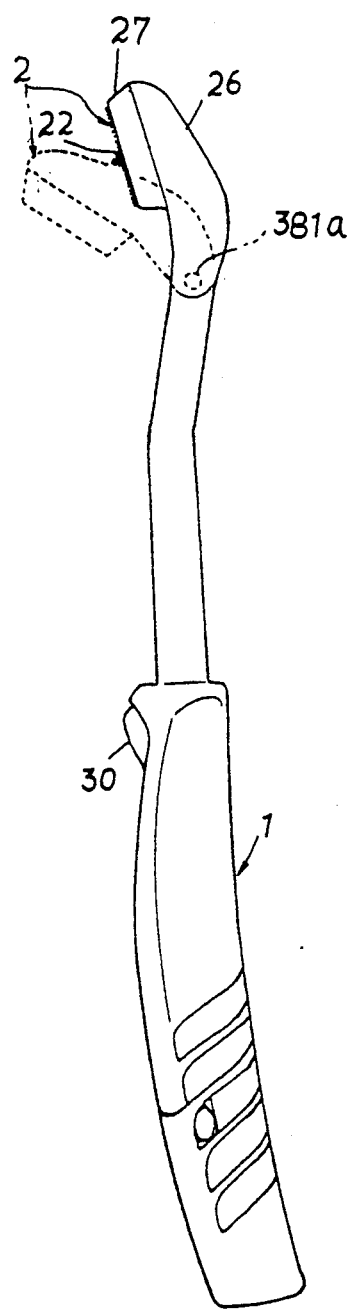
FIG. 4 is an illustration showing a rotating bristle holder of the toothbrush as shown in FIG. 3.

Another preferred embodiment of the present invention is shown in FIGS. 3, 3a and 4, in which the driving means 3 is modified to include: a driving gear 33a formed as a bevel gear secured on a motor shaft of the driving motor 32, a follower gear 37 also formed as a bevel gear engageable with the driving gear 33a pivotally secured in the grip portion 1a by a gear pivot 371 having a gear pulley 372 secured on the gear pivot 371, a transmission belt 36 generally formed as a loop having a lower belt end 361 wound on the gear pulley 372 and an upper belt end 362 wound on a bristle-rotating wheel 25a secured with the axle portion 23 of the bristle base portion 21 mounted with the bristles 22 and a plurality of pairs of idler pulleys 38 pivotally secured in the cavity 11 of the handle 1 by a plurality of pivots 381, 381a for guiding the belt 36 on the idler pulleys 38. The pivot 381a will serve for pivotally coupling the bristle holder means 2 with the handle 2 to allow the bristle holder means 2 to be rotated about the pivot 381a for adjusting its rotating angle in relation to the handle 1 as shown in FIG. 4.

The present invention can be suitably modified and the disclosure is in no way limited to the preferred embodiments as described and shown.

The bristles 22 and the bristle base portion 21 may be replaceably mounted in the bristle holder 26 so that when the bristle are worn or damaged, the base portion 21 and bristles 22 may be replaced with a new set for an easy maintenance purpose.

In order for rinsing the bristles 22 of this invention, a water hole (not shown) may be drilled in the bristle holder means 2 to direct water into the bristle base portion 21 for flushing and cleaning the bristles 22.

I claim:

1. A toothbrush comprising:
 a handle having an inner cavity longitudinally formed inside the handle;
 a bristle holder means rotatably secured on one end portion of said handle and having a plurality of bristles mounted on a bristle base portion rotatably held in said bristle holder means; and
 a driving means formed in said inner cavity of said handle operatively driving said bristle base portion for rotating said bristles on a tooth surface or in an aperture between two neighbouring teeth for cleaning the same;
 said bristle holder means including: the bristle base portion having a plurality of said bristles mounted thereon, an axle portion protruding downwardly from the bristle base portion to be rotatably mounted in an axle hole formed in a supporting plate secured on a bristle holder, a packing ring sealably disposed around the axle portion and the axle hole of the supporting plate, a follower gear formed as a bevel gear secured with the axle portion rotatably held in a bristle socket formed in a head portion of the bristle holder, the bristle holder having a central hole formed therethrough and having a lower end portion of said bristle holder rotatably coupled with an upper end portion of the handle, and a soft protective wall having a height lower than a height of the bristle and circumferentially disposed on the head portion for enclosing the bristles within said protective wall;
 the improvement which comprises:
 said plurality of bristles including a first portion of said bristles forming a central vertex bristle portion and a second portion of said bristles forming a peripheral bristle portion surrounding the central vertex portion and mounted in a spiral arrangement on said bristle base portion, whereby upon a rotation of said bristle base portion, the bristles of said central vertex portion will penetrate into apertures between the teeth and the bristles of said peripheral bristle portion will rotatably brush the teeth surfaces for effectively cleaning the teeth.

2. A toothbrush according to claim 1, wherein said driving means includes: a power source stored in a lower portion of the inner cavity of said handle, a driving motor electrically connected with the power source and controlled by a switch formed on the handle, a motor shaft rotatably driven by the driving motor, a transmission shaft connected with the motor shaft and rotatably secured in the handle and protruding upwardly inside the inner cavity and the central hole in the bristle holder, and a driving gear formed as a bevel gear formed on an upper end of the transmission shaft engageable with the follower gear of the bristle holder means for rotatably driving said bristle base portion and said bristles, said transmission shaft being a flexible transmission shaft coupled to said motor shaft.

3. A toothbrush comprising:
 a handle having an inner cavity longitudinally formed inside the handle;
 bristle holder means rotatably secured on one end portion of said handle and having a plurality of bristles mounted on a bristle base portion rotatably held in said bristle holder means; and
 a driving means formed in said inner cavity of said handle operatively driving said bristle base portion for rotating said bristle son a tooth surface or in an aperture between two neighbouring teeth for cleaning the same;
 said bristle holder means including: the bristle base portion having a plurality of said bristles mounted thereon, an axle portion protruding downwardly from the bristle base portion to be rotatably mounted in an axle hole formed in a supporting plate secured on a bristle holder, a packing ring sealably disposed around the axle portion and the axle hole of the supporting plate, a bristle-rotating wheel secured with the axle portion rotatably held in a bristle socket formed in a head portion of the bristle holder, the bristle holder having a central hole formed therethrough and having a lower end portion of said bristle holder rotatably coupled with an upper end portion of the handle, and a soft protective wall having a height lower than a height of the bristle and circumferentially disposed on the head portion for enclosing the bristles within said protective wall;
 said driving means including: a driving gear formed as a bevel gear secured on a motor shaft of a driving motor mounted in the handle, a follower gear formed as a bevel gear engageable with the driving gear rotatably secured in a grip portion of the handle by a gear pivot having a gear pulley secured on the gear pivot, a transmission belt generally formed as a loop having a lower belt end wound on the gear pulley and an upper belt end wound on the bristle-rotating wheel secured with the axle portion of the bristle base portion mounted with the bristles thereon, and a plurality of pairs of idler pulleys pivotally secured in the inner cavity of the handle for guiding said belt, whereby upon a rotation of said driving motor for rotating the driving gear and the follower gear, said transmission belt will rotate said bristle rotating wheel, said bristle base portion and bristles; and the improvement which comprises:

said plurality of bristles including a first portion of said bristles forming a central vertex bristle portion and a second portion of said bristles forming a peripheral bristle portion surrounding the central vertex portion and mounted in a spiral arrangement on said bristle base portion, whereby upon a rotation of said bristle base portion, the bristles of said central vertex portion will penetrate into apertures between the teeth and the bristles of said peripheral bristle portion will rotatably brush the teeth surface for effectively cleaning the teeth.

* * * * *